United States Patent [19]

Foulletier

[11] 4,418,004
[45] Nov. 29, 1983

[54] CATALYSTS FOR GASEOUS PHASE FLUORINATION OF ALIPHATIC CHLORINATED AND CHLOROFLUORINATED DERIVATIVES

[75] Inventor: Louis Foulletier, Oullins, France

[73] Assignee: PCUK Produits Chimiques Ugine Kuhlmann, Courbevoie, France

[21] Appl. No.: 324,439

[22] Filed: Nov. 24, 1981

[30] Foreign Application Priority Data

Dec. 29, 1980 [FR] France ................ 80 27660

[51] Int. Cl.$^3$ ............................ B01J 27/02
[52] U.S. Cl. .................. 502/182; 570/165; 502/217
[58] Field of Search ............ 252/440; 570/165

[56] References Cited

U.S. PATENT DOCUMENTS

| | | | |
|---|---|---|---|
| 2,110,369 | 3/1938 | Leicester | 570/168 |
| 2,115,874 | 5/1938 | Rehm | 252/440 X |
| 2,210,369 | 8/1940 | Herbst | 240/7.6 |
| 2,458,551 | 1/1949 | Benning et al. | 260/653 |
| 3,600,450 | 8/1971 | Kaess et al. | 252/440 X |

FOREIGN PATENT DOCUMENTS

| | | |
|---|---|---|
| 720474 | 12/1931 | France . |
| 2000688 | 9/1969 | France . |
| 50-144690 | 11/1975 | Japan .................. 252/440 |

*Primary Examiner*—William G. Wright
*Attorney, Agent, or Firm*—Pennie & Edmonds

[57] ABSTRACT

This invention relates to improved catalysts for gaseous phase fluorination of aliphatic chlorinated and chlorofluorinated derivatives by hydrofluoric acid. The catalysts are characterized by an active carbon support having a total specific surface area greater than about 1000 m$^2$/g but less then about 2000 m$^2$/g, a surface area of pores of 40 to 50 Å in radius above about 5 m$^2$/g but less then about 15 m$^2$/8, a surface area of pores greater than or equal to 250 Å in radius above about 2 m$^2$/g but less than about 6 m$^2$/g, which has been impregnated with an aqueous chromium sulfate solution and dried. This invention also relates to gaseous phase fluorination processes for chlorinated or chlorofluorinated derivatives utilizing these catalysts in fluidized bed reactors.

5 Claims, No Drawings

CATALYSTS FOR GASEOUS PHASE FLUORINATION OF ALIPHATIC CHLORINATED AND CHLOROFLUORINATED DERIVATIVES

TECHNICAL FIELD

This invention relates to improved catalysts for gaseous phase fluorination of aliphatic chlorinated and chlorofluorinated derivatives by hydrofluoric acid. The catalysts are characterized by an active carbon support impregnated with chromium sulfate.

This invention also relates to gaseous phase fluorination processes of chlorinated or chlorofluorinated derivatives utilizing these chromium sulfate catalysts in fluidized bed reactors.

BACKGROUND ART

Various catalysts which substitute fluorine atoms for chlorine atoms have been proposed for use in gaseous phase reactions. Frequently, these catalysts are oxides or halides of chromium, aluminum, cobalt, iron, titanium, nickel, copper, palladium or zirconium; which may be supported on active carbon or alumina. French Pat. No. 720,474 and its Certificate of Addition No. 43.972 teach gaseous phase fluorination of hydrocarbons containing a halogen other than fluorine, by metallic halide catalysts.

U.S. Pat. No. 2,110,369 discloses the fluorination of $C_1$ to $C_3$ halohydrocarbons over catalysts having a chromium halide base deposited on coke or active carbon.

U.S. Pat. No. 2,458,551 describes a catalyst prepared by impregnating active carbon with chromium trichloride and subsequently heating the product with hydrofluoric acid under anhydrous conditions.

To obtain trichlorotrifluoroethane and dichlorotetrafluoroethane with small amounts os asymmetric isomers, French Pat. No. 2.000.688 teaches the use of pure chromium trifluoride or chromium trifluoride supported on wood charcoal, petroleum coke or coal carbon as a catalyst for the reaction of tetrachloroethylene with chlorine and hydrofluoric acid.

These commonly used chromium halide catalysts deposited on carbon supports are basically suitable for gaseous phase fluorination of chloroalkanes or chlorofluoroalkanes in fixed bed reactor systems. In fluidized bed reactors, which require regular-shaped particles and homogeneous granulometry, the prior art catalysts are inadequate and inefficient for use in fluorination processes. Simple grinding of the catalysts, followed by shifting for the selection of suitable-sized particles provides irregularly-shaped grains which are not suitable for use in fluidized bed reactors. Consequently, their use leads to a significant loss of the catalyst, which necessitates recharging the reactor at various intervals during the process.

The prior art catalysts often demonstrate at least one of the following disadvantages:
low rate of conversion of hydrofluoric acid
low productivity
low selectivity
low activity in the fluorination of chlorinated derivatives other than chlorocarbons, and especially in the fluorination of chlorinated nitriles.

SUMMARY OF THE INVENTION

This invention discloses gaseous phase fluorination catalysts for chlorinated and chlorofluorinated aliphatic derivatives. The catalaysts are characterized in that an active carbon is impregnated with chromium sulfate. The catalysts are prepared by impregnating active carbon having a total specific surface area greater than about 1000 $m^2/g$ but less than about 2000 $m^2/g$, and high mesoporosity and microporosity, with an aqueous solution of chromium sulfate. Preferably, the catalyst comprises about 0.5 to 1.5 atoms/g of chromium per liter and is the form of particles of about 100 $\mu m$ to 3,000 $\mu m$ in diameter.

The applicant has discovered that gaseous phase fluorination catalysts are frequently tainted by the formation of tar on their surfaces and that the use of gaseous phase fluorination catalysts in fluidized bed reactors is advantageous since they cause abrasion of the catalyst grains, thus eliminating any attached tar and promoting catalytic activity. The catalyst is uniquely consumed by attrition and there is no need to stop the reaction in order to recharge the reactor with the catalyst.

DETAILED DESCRIPTION OF THE INVENTION

The gaseous phase fluorination catalysts of this invention comprise an active carbon support having a total specific surface area greater than about 1000 $m^2/g$, but less than about 2000 $m^2/g$ which is impregnated with an aqueous chromium sulfate solution and subsequently dried at a temperature of, advantageously, about 150° C.

The mesoporosity of the carbon support, defined by a surface area of pores of 40 to 50 Å in radius, should by greater than about 5 $m^2/g$ but less than about 15 $m^2/g$. The macroporosity of the support, defined by a surface area of pores equal to or above 250 Å in radius, should be greater than about 2 $m^2/g$ but less than about 6 $m^2/g$.

The choice of chromium salt anion for the impregnation of active carbon is especially critical for the specificity of the catalyst. Unexpectedly, the sulfate ions provide catalysts which give excellent yields when used for the fluorination of aliphatic chlorinated or chlorofluorinated hydrocarbons or aliphatic chlorinated nitriles, such as trichloroacetonitrile.

According to an alternate embodiment of this invention, the active carbon support is impregnated with an aqueous solution of chromium trioxide ($CrO_3$) containing sulfuric acid, rather than chromium sulfate. At least part of the hexavalent chromium is reduced to trivalent chromium by the active carbon.

EXAMPLES

The following examples demonstrate various methods of preparing the catalysts of this invention and uses of the catalysts in various fluorination reactions. The examples are set forth for the purpose of illustration only and are not to be construed as limiting the scope of the invention in any manner.

EXAMPLE 1

A wood charcoal support having the following characteristics is used:

| | |
|---|---|
| Density | 0.55 $g/cm^3$ |
| Total Specific Surface Area | 1,200 $m^2/g$ |
| Surface Area of Pores Having a Radius $\geq$ 250 Å | 3 $m^2/g$ |
| Surface Area of Pores Having a Radius = 40–50 Å | 9 $m^2/g$ |

The active carbon is impregnated with an aqueous solution of pure chromium sulfate at a concentration of 600 g/l so that the resulting product comprises 1 atomg of chromium per liter of catalyst. The catalyst is dried by air in a fluidized bed at a temperature of 150° C.

The catalyst is advantageously used for the gaseous phase fluorination of trichlorotrifluoroethane into dichlorotetrafluoroethane, in a fluidized bed under the following conditions:

| Molar Ratio HF/$C_2Cl_3F_3$ | 1.02/1 |
|---|---|
| Flow Rate | 18 moles/h/l |
| Temperature | 400° C. |

The conversion rate of hydrofluoric acid is 75% and the dichlorotetrafluoroethane obtained contains 85% symmetric isomer.

EXAMPLE 2

Using the active carbon of Example 1, a catalyst containing 0.75 atoms/g of chromium per liter is prepared under similar conditions. The catalyst is used for the fluorination of trichlorotrifluoroethane into dichlorotetrafluoroethane in a fluidized bed under the following conditions:

| Molar Ratio HF/$C_2Cl_3F_3$ | 1.45/1 |
|---|---|
| Flow Rate | 11 moles/h/l |
| Temperature | 400° C. |

The conversion rate of hydrofluoric acid is 67% and the dichlorotetrafluoroethane obtained contains 85% symmetric isomer.

EXAMPLE 3

The catalyst of Example 1 is used in the fluorination of hexachloroethane, formed in situ by the reaction of chlorine on tetrachloroethylene under the following conditions:

| Molar Ratio HF/$Cl_2$/$C_2Cl_4$ | 3.97/1.2/1 |
|---|---|
| Flow Rate | 18.39 moles/h/l |
| Temperature | 400° C. |

The conversion rate of hydrofluoric acid is 67%. The conversion rates of tetrachloroethylene are:
44.6% into trichlorotrifluoroethane, containing 98.5% symmetric isomer
38.3% into dichlorotetrafluoroethane, containing 82.7% symmetric isomer.

EXAMPLE 4 (COMPARATIVE EXAMPLE)

Following the data recorded in French Pat. No. 2,000,688, 100 g of active carbon, derived from petroleum and marketed under the trademark "Columbia CXC", is impregnated with a solution of 61 g hydrated chromium trichloride ($CrCl_3 \cdot 6H_2O$) in 200 g of water. The catalyst is dried at 110° C.

The catalyst is used for the fluorination of hexachloroethylene formed in situ under the following conditions:

| Molar Ratio HF/$Cl_2$/$C_2Cl_4$ | 4.3/1.2/1 |
|---|---|
| Flow Rate | 13/moles/h/l |
| Temperature | 400° C. |

The conversion rate of hydrofluoric acid is only 32.5%. The conversion rates of tetrachloroethylene are:
44.5% into trichlorotrifluoroethane, containing 57% symmetric isomer
1.4% into dichlorotetrafluoroethane, containing 43% symmetric isomer.

EXAMPLE 5

The catalyst of Example 1 is used in the fluidized bed fluorination of trichloroacetonitrile, under the following conditions:

| Molar Ratio HF/$CCl_3CN$ | 5.36/1 |
|---|---|
| Flow Rate | 4.55 moles/h/l |
| Temperature | 400° C. |

The conversion rate of hydrofluoric acid is 49.9%.
The conversion rates of trichloroacetonitrile are:
45.2% into trifluoroacetonitrile
28.4% into chlorodifluoroacetonitrile.

EXAMPLE 6

1 liter of the active carbon of Example 1 is impregnated with 400 cm$^3$ of an aqueous solution containing 1.0 mole of chromium trioxide ($CrO_3$) and 1.83 mole of sulfuric acid. The entire solution is adsorbed by the active carbon. The catalyst is dried in a fluidized bed at 150° C.

The catalyst is used for the fluidized bed fluorination of trichloroacetonitrile, under the following conditions:

| Molar Ratio HF/$CCl_3CN$ | 6.95/1 |
|---|---|
| Flow Rate | 5.71 moles/h/l |
| Temperature | 400° C. |

The conversion rate of hydrofluoric acid is 38.7%.
The conversion rates of trichloroacetonitrile are:
54.1% into trifluoroacetonitrile
24.9% into chlorodifluoroacetonitrile.

EXAMPLE 7

This example demonstrates the critical role of the sulfate ($SO_4^{--}$) ions in the catalyst's promotion of the fluorination of trichloroacetonitrile.

A catalyst similar to that in Example 6 is prepared by impregnating 1 liter of the active carbon of Example 1 with 400 cm$^3$ of an aqueous solution of 2.5 moles of chromium trioxide, not containing any sulfuric acid. The entire solution is adsorbed by the carbon. The catalyst is dried in a fluidized bed at 150° C.

The catalyst is used in the fluorination of trichloroacetonitrile in a fluidized bed, under the following conditions:

| Molar Ratio HF/$CCl_3CN$ | 4.95/1 |
|---|---|
| Flow Rate | 4.2 moles/h/l |
| Temperature | 400° C. |

The conversion rate of hydrofluoric acid is only 21.8%. The conversion rates of trichloroacetonitrile are:

2.8% into trifluoroacetonitrile
7.7% into chlorodifluoroacetonitrile.

I claim:

1. A catalyst comprising active carbon impregnated with chromium sulfate, wherein the active carbon comprises:
   (a) a specific surface area greater than about 1000 m$^2$/g, but less than about 2000 m$^2$/g
   (b) a surface area of pores of 40 to 50 Å in radius which is greater than about 5 m$^2$/g, but less than about 15 m$^2$/g
   (c) a surface area of pores equal to or above 250 Å in radius which is greater than about 2 m$^2$/g, but less then about 6 m$^2$/g.

2. A catalyst according to claim 1, wherein the catalyst comprises about 0.5 to 1.5 atoms/g of chromium per liter.

3. A catalyst according to claim 2, wherein the catalyst is in the form of particles between about 100 μm to 3,000 μm in diameter.

4. A process for the preparation of a catalyst comprising active carbon impregnated with chromium sulfate comprising the steps of:
   (a) impregnating, by means of an aqueous chromium sulfate solution, an active carbon comprising:
      (1) a specific surface area greater than about 1000 m$^2$/g; but less than about 2000 m$^2$/g
      (2) a surface area of pores of 40 to 50 Å in radius which is greater than about 5 m$^2$/g; but less than about 15 m$^2$/g
      (3) a surface area of pores equal to or above 250 Å in radius which is greater than about 2 m$^2$/g but less than about 6 m$^2$/g ; and
   (b) drying the impregnated carbon.

5. A process for the preparation of a catalyst comprising active carbon impregnated with chromium sulfate comprising the steps of:
   (a) impregnating, by means of an aqueous solution of chromium trioxide containing sulfuric acid, an active carbon comprising:
      (1) a specific surface area greater than about 1000 m$^2$/g; but less then about 2000 m$^2$/g
      (2) a surface area of pores of 40 to 50 Å in radius which is greater than about 5 m$^2$/g; but less than about 15 m$^2$/g
      (3) a surface area of pores equal to or above 250 Å in radius which is greater than about 2 m$^2$/g; but less than about 6 m$^2$/g
   (b) drying the impregnated carbon.

* * * * *

UNITED STATES PATENT AND TRADEMARK OFFICE
CERTIFICATE OF CORRECTION

PATENT NO. : 4,418,004
DATED : November 29, 1983
INVENTOR(S) : Louis Foulletier

It is certified that error appears in the above—identified patent and that said Letters Patent is hereby corrected as shown below:

Abstract, line 8, reads "15m2/8" should read --15m2/g--.

Column 1, line 37, reads "os", should read --of--.

Column 3, line 3, reads "atomg", should read --atom/g--.

Signed and Sealed this

Fifteenth Day of May 1984

[SEAL]

Attest:

GERALD J. MOSSINGHOFF

Attesting Officer

Commissioner of Patents and Trademarks